United States Patent [19]

Harde et al.

[11] Patent Number: 5,089,044
[45] Date of Patent: Feb. 18, 1992

[54] SUBSTITUTED PYRIMIDINYLOXY(THIO)- AND TRIAZINYLOXY (THIO)ACRYLIC ACID DERIVATIVES, PROCESSES FOR THEIR PREPARATION AND THEIR USE AS HERBICIDES, FUNGICIDES AND PLANT GROWTH REGULATORS

[75] Inventors: Christoph Harde; Erhard Nordhoff; Anita Krüger; Gabriele Krüger; Gerhard Tarara; Peter Wegner; Nikolaus Heinrich; Clemens Kötter; Gerhard Johann; Richard Rees, all of Berlin, Fed. Rep. of Germany

[73] Assignee: Schering Aktiengesellschaft, Fed. Rep. of Germany

[21] Appl. No.: 555,585

[22] Filed: Jul. 19, 1990

[30] Foreign Application Priority Data

Jul. 19, 1989 [DE] Fed. Rep. of Germany ....... 3924260

[51] Int. Cl.$^5$ .................... A01N 43/54; A01N 43/66; C07D 239/60; C07D 251/38
[52] U.S. Cl. .......................... 71/90; 71/92; 71/93; 544/194; 544/204; 544/209; 544/210; 544/211; 544/212; 544/213; 544/215; 544/216; 544/217; 544/218; 544/219; 544/300; 544/301; 544/302; 544/310; 544/312; 544/313; 544/314; 544/316; 544/317; 544/318
[58] Field of Search ............... 544/300, 301, 302, 310, 544/312, 313, 314, 316, 317, 318; 71/90, 92

[56] References Cited

U.S. PATENT DOCUMENTS

| | | | |
|---|---|---|---|
| 4,847,259 | 7/1989 | Kisida et al. | 544/318 |
| 4,968,340 | 11/1990 | Kaku et al. | 544/318 |
| 4,973,354 | 11/1990 | Hatanaka et al. | 544/314 |

OTHER PUBLICATIONS

Acheson et al, *Chemical Abstracts*, vol. 94, No. 192220 (1981).

*Primary Examiner*—Nicholas S. Rizzo
*Assistant Examiner*—E. Bernhardt
*Attorney, Agent, or Firm*—Ostrolenk, Faber, Gerb & Soffen

[57] ABSTRACT

The invention relates to new substituted pyrimidinyloxy(thio)- and triazinyloxy(thio)acrylic acid derivative of general formula I

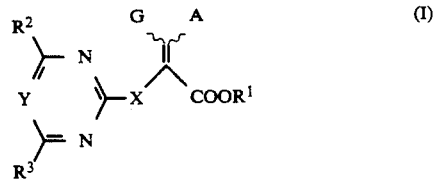

in which A, G, $R^{1-3}$, X and Y have the meanings given in the description, processes for their preparation and their use as herbicides, fungicides and plant growth regulants.

17 Claims, No Drawings

SUBSTITUTED PYRIMIDINYLOXY(THIO)- AND TRIAZINYLOXY (THIO)ACRYLIC ACID DERIVATIVES, PROCESSES FOR THEIR PREPARATION AND THEIR USE AS HERBICIDES, FUNGICIDES AND PLANT GROWTH REGULATORS

DESCRIPTION

This invention relates to new substituted pyrimidinyloxy(thio)- and triazinyloxy(thio)acrylic acid derivatives, processes for their preparation and their use as herbicides, fungicides and plant growth regulators.

It is known that pyrimidine derivatives possess herbicidal activity (EP 223 406, 249 707, 249 708, 287 072 and 287 079). However, the herbicidal activity of these known compounds is often insufficient or selectivity problems are seen in important crops.

The object of the present invention is to make new compounds that do not have these disadvantages and have improved biological properties over the known compounds.

It has now been found that substituted pyrimidinyloxy(thio)- and triazinyloxy(thio)acrylic acid derivatives of general formula I

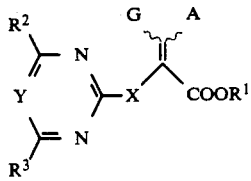

in which

A is one of the groups A-1 to A-6 of general formula

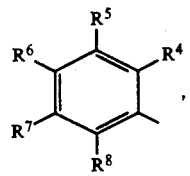 A-1

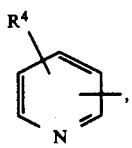 A-2

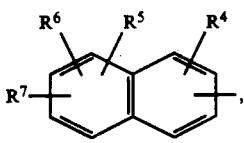 A-3

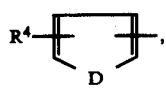 A-4

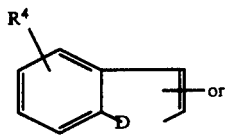 A-5 or

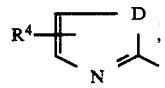 A-6 a $C_1$-$C_{10}$-alkyl, $C_2$-$C_{10}$-alkenyl or $C_2$-$C_{10}$-alkynyl group (each of which is optionally substituted by one or more of the same or different $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl), or a $C_3$-$C_8$-cycloalkyl or $C_4$-$C_8$-cycloalkenyl group (each of which is optionally substituted by one or more of the same or different $C_1$-$C_4$-alkyl, $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl);

D is oxygen, sulphur or the group —$NR^9$—;

G is hydrogen or $C_1$-$C_6$-alkyl;

$R^1$ is hydrogen, $C_1$-$C_4$-alkyl or benzyl;

$R^2$ and $R^3$, which may be the same or different, are $C_1$-$C_4$-alkyl, $C_1$-$C_4$-alkoxy, $C_1$-$C_4$-alkylthio, $C_1$-$C_4$-alkylamino, di-$C_1$-$C_4$-alkylamino or halogen;

$R^4$, $R^5$, $R^6$, $R^7$ and $R^8$, which may be the same or different, are hydrogen, $C_1$-$C_4$-alkyl, $C_1$-$C_4$-alkoxy, amino, di-$C_1$-$C_4$-alkylamino, nitro, halogen, trifluoromethyl or phenyl;

$R^9$ is hydrogen, $C_1$-$C_4$-alkyl or phenyl;

X is oxygen or sulphur; and

Y is methine or nitrogen, as well as their alkali metal, alkaline earth metal and organic ammonium salts, and their E- and Z-isomers, show interesting herbicidal, fungicidal and plant growth regulant activity.

The expression "halogen" means fluorine, chlorine, bromine and iodine. By the term alkali metal is meant lithium, sodium or potassium and by the term alkaline earth metal is meant calcium, strontium or barium.

The compounds of the invention of general formula I can be prepared for example by reacting a compound of general formula II

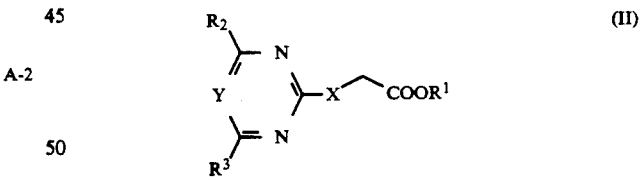

in which $R^1$, $R^2$ and $R^3$, X and Y have the meanings given under general formula I, with a compound of general formula III

in which A and G have the meanings given under general formula I, in a suitable solvent in the presence of a suitable base, and if desired a compound of general formula I in which $R^1$ is hydrogen, $C_1$-$C_4$-alkyl or benzyl, so obtained, is reacted with an alkali metal base, an alkaline earth metal base or an organic ammonium base, in a suitable polar solvent, to give a compound of general formula I in which $R^1$ is an alkali metal atom, one equivalent of an alkaline earth metal atom or an organic ammonium group, and/or if desired, a compound of formula I in which $R^1$ is $C_1$-$C_4$-alkyl, benzyl or an alkali metal atom, one equivalent of an alkaline earth metal atom or an organic ammonium group, is reacted with a suitable acid in a suitable solvent to give a compound of general formula I in which $R^1$ is hydrogen.

The individual process variants are preferably carried out in the presence of a diluent. For this, a solvent which is inert to the reactants is used.

Suitable solvents include water, aliphatic, alicyclic and aromatic hydrocarbons, that can be optionally chlorinated, such as for example hexane, cyclohexane, petroleum ether, ligroin, benzene, toluene, xylene, methylene chloride, chloroform, carbon tetrachloride, ethylene chloride and trichloroethane, ethers, such as for example diisopropyl ether, dibutyl ether, propylene oxide, dioxane and tetrahydrofuran; ketones, such as for example acetone, methyl ethyl ketone, methyl isopropyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide, and bases, such as for example pyridine.

The presence of a catalyst can be an advantage. Suitable catalysts include potassium iodide and onium compounds, such as quaternary ammonium, phosphonium and arsonium compounds as well as sulphonium compounds. Also suitable are polyglycol ethers, especially cyclic ethers, such as 18-crown-6, and tertiary amines, such as for example tributylamine. Preferred compounds are quaternary ammonium compounds, such as for example benzyltriethylammonium chloride and tetrabutylammonium bromide.

The reactions can be carried out under atmospheric pressure but if desired higher or lower pressures can be used.

The main process variant is preferably carried out in an aprotic solvent such as benzene, toluene, xylene, tetrahydrofuran, diethyl ether, hexane, dimethylformamide or dimethyl sulphoxide.

Bases that can be used include sodium hydride, potassium tert-butylate or lithium diisopropylamide.

The reactions are suitably carried out between $-78°$ C. and the boiling point of the particular solvent or solvent mixture.

The reaction usually takes 5 minutes to 48 hours, preferably 0.5 to 24 hours.

Compounds of general formula II are described in the literature or can be prepared by methods analogous to those described in the literature. (Khim.-Farm. Zh. 16 (8), 931-4 [1982]; Ukr. Khim. Zh. (Russ. Ed) 49 (11), 1205-8 [1983]; Fizol. Akt. Veshchestva 18. 75-9 [1986]; and USSR Patent 791746).

For the optional subsequent processes there is preferably used as a solvent an alcohol, such as ethanol, propanol or isopropanol, a ketone, such as acetone or methyl ethyl ketone, dimethylformamide or dimethyl sulphoxide, water or solvent/water mixtures.

Alkaline metal bases, alkaline earth metal bases or organic ammonium bases that can be used include for example, carbonates, such as sodium carbonate, potassium carbonate or calcium carbonate, metal hydroxides, such as sodium hydroxide, potassium hydroxide, barium hydroxide or strontium hydroxide and as organic ammonium bases, ammonium derivatives, alkylamines (primary amines), dialkylamines (secondary amines) or trialkylamines (tertiary amines).

Examples of acids are hydrochloric or sulphuric acid.

The reaction temperature lies between room temperature and the boiling point of the particular solvent. The reaction time lies between 0.5 to 48 hours. When converting an ester in which $R^1$ is benzyl to the free acid a catalytic reduction (hydrogenation) can also be used.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractional distillation or crystallisation.

The compounds of the invention are, as a rule, colourless and odourless liquids or crystals that are soluble in water, slightly soluble in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons, such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of the invention show a good herbicidal activity in broad leaved weeds and grasses. A selective use in various crops is possible, for example in such as rape, beets, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops.

The compounds of the invention can used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.001 and 5 kg/ha.

The compounds of the invention can also be used as defoliants, desiccants and as total herbicides. They also influence plant growth and can thus be used to influence plant growth of crops. Some compounds also show fungicidal activity.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 38, No. 3 (1989) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talc, kaolin, attapulgite, limestone, silicic acid and plant products, e.g. flours.

As surface-active agents there can be used for example calcium lignosulphonate, polyoxyethylenealkylphenyl ethers, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable Powder
  1)
    25 percent by weight active ingredient
    60 percent by weight kaolin
    10 percent by weight silicic acid
    5 percent by weight of a mixture of calcium lignosulphonate and the sodium salt of N-methyl-N-oleyltaurine
  2)
    40 percent by weight active ingredient
    25 percent by weight bentonite
    25 percent by weight colloidal silicic acid
    10 percent by weight of a mixture of calcium lignosulphonate and alkylphenyl polyglycol ether B) Paste
    45 percent by weight active ingredient
    5 percent by weight sodium aluminium silicate
    15 percent by weight cetyl polyglycol ether with 8 mol of ethylene oxide
    2 percent by weight spindle oil
    10 percent by weight polyethylene glycol
    23 percent by weight water C) Emulsifiable Concentrate
    25 percent by weight active ingredient
    15 percent by weight cyclohexanone
    55 percent by weight xylene
    5 percent by weight of a mixture of calcium dodecylbenzenesulphonate and nonylphenolpolyoxyethylene.

The following Examples illustrate the preparation of compounds of the invention.

EXAMPLE 1

Methyl 2-(4,6-dimethoxy-2-pyrimidinylthio)-3-phenylacrylate 2.8 g (28.7 mmol) Diisopropylamine was dissolved in 80 ml tetrahydrofuran under nitrogen and treated with 11.5 ml (28.7 mmol) 2.5M n-butyllithium in hexane at a temperature between −78° and −50° C. The mixture was stirred for 10 minutes and then a solution of 7 g (28.7 mmol) methyl 2-(4,6-dimethoxy-2-pyrimidinylthio)acetate in 80 ml tetrahydrofuran was added to the reaction mixture and the mixture then stirred for 20 minutes. 2.8 g (28.7 mmol) Benzaldehyde was added, dropwise, to the solution. The reaction mixture was slowly allowed to reach room temperature, with stirring, and then stirred for 16 hours. The precipitate was treated with 500 ml water and extracted with ethyl acetate. The ethyl acetate phase, after drying over magnesium sulphate, was evaporated and then purified by medium pressure chromatography using hexane/ethyl acetate as eluent.

Yield: 6.1 g = 63.9% of theory
$n_D^{20}$: 1.5926

PREPARATION OF THE STARTING MATERIAL

Methyl 2-(4,6-dimethoxy-2-pyrimidinylthio)acetate 25 g (230 mmol) Methyl thioglycolate was dissolved in 250 ml dimethylformamide and treated with 16.3 g (115 mmol) potassium carbonate. After 20 minutes stirring at room temperature, 50 g (2.3 mmol) 4,6-dimethoxy-2-methylsulphonylpyrimidine was added and the mixture heated for 3 hours at 90° C. The reaction mixture was then poured into water and extracted with ethyl acetate. The organic phase was washed with water and dried over magnesium sulphate. The solvent was distilled and the resulting crude product was recrystallised from diisopropyl ether.

Yield: 44.6 g = 79.4% of theory
mp: 67°–69° C.

EXAMPLE 2

2-(4,6-dimethoxy-2-pyrimidinylthio)-3-phenylacrylic acid 0.5 g (1.5 mmol) Methyl 2-(4,6-dimethoxy-2-pyrimidinylthio)-3-phenylacrylate and 95 mg (1.7 mmol) potassium hydroxide were added to a mixture of 5 ml water and 5 ml ethanol and the mixture heated at 50° C. for 8 hours. It was then diluted with about 100 ml water and extracted with ethyl acetate. The aqueous phase was acidified with 10% hydrochloric acid until it was pH 2 and extracted with ethyl acetate. After drying the ethyl acetate phase over magnesium sulphate, the solvent was evaporated under reduced pressure and the residue recrystallised from diisopropyl ether.

Yield: 0.25 g=52% of theory mp: 162°–164° C.

In a similar manner, the following compounds of formula I were prepared:

| Example No. | A | G | $R^1$ | $R^2$ | $R^3$ | X | Y | Physical constant |
|---|---|---|---|---|---|---|---|---|
| 3 | 2-Furyl | H | $CH_3$ | $OCH_3$ | $OCH_3$ | S | CH | mp.: 106–108° C. |
| 4 | 2-Furyl | H | H | $OCH_3$ | $OCH_3$ | S | CH | mp.: 133–136° C. |
| 5 | 2-Thienyl | H | $CH_3$ | $OCH_3$ | $OCH_3$ | S | CH | mp.: 106–109° C. |
| 6 | 2-Thienyl | H | H | $OCH_3$ | $OCH_3$ | S | CH | mp.: 176° C. (dec.) |
| 7 | 2-Nitrophenyl | H | $CH_3$ | $OCH_3$ | $OCH_3$ | S | CH | mp.: 162–164° C. |
| 8 | 2-Nitrophenyl | H | H | $OCH_3$ | $OCH_3$ | S | CH | mp.: 215° C. (dec.) |
| 9 | 1-Naphthyl | H | $CH_3$ | $OCH_3$ | $OCH_3$ | S | CH | mp.: 95–96° C. |
| 10 | 2-Naphthyl | H | $CH_3$ | $OCH_3$ | $OCH_3$ | S | CH | mp.: 98–99° C. |
| 11 | $CH_3CH=CH-$ | H | $CH_3$ | $OCH_3$ | $OCH_3$ | S | CH | mp.: 40–42° C. |
| 12 | $CH_3CH_2-$ | H | $CH_3$ | $OCH_3$ | $OCH_3$ | S | CH | $n_D^{20}$: 1.5431 |
| 13 | 2-Naphthyl | H | H | $OCH_3$ | $OCH_3$ | S | CH | mp.: 159–161° C. |
| 14 | 1-Naphthyl | H | H | $OCH_3$ | $OCH_3$ | S | CH | mp.: 180–182° C. |
| 15 | $H_2C=CH-$ | H | $CH_3$ | $OCH_3$ | $OCH_3$ | S | CH | mp.: 40–43° C. |
| 16 | $CH_3CH_2CH_2-$ | H | $CH_3$ | $OCH_3$ | $OCH_3$ | S | CH | $n_D^{20}$: 1.5381 |
| 17 | Phenyl | H | $CH_3$ | $OCH_3$ | $N(CH_3)_2$ | S | N | mp.: 107–108° C. |
| 18 | $(CH_3)_2CH-$ | H | $CH_3$ | $OCH_3$ | $OCH_3$ | S | CH | mp.: 50–53° C. |
| 19 | 2-Phenylethyl | H | $CH_3$ | $OCH_3$ | $OCH_3$ | S | CH | $n_D^{20}$: 1.5711 |
| 20 | Phenyl | H | H | $OCH_3$ | $N(CH_3)_2$ | S | N | mp.: 156–158° C. |
| 21 | $CH_3CH_2CH_2-$ | H | H | $OCH_3$ | $OCH_3$ | S | CH | mp.: 108–111° C. |
| 22 | $(CH_3)_2CH-$ | H | H | $OCH_3$ | $OCH_3$ | S | CH | mp.: 100–103° C. |
| 23 | $CH_3-$ | H | $CH_3$ | $OCH_3$ | $OCH_3$ | O | CH | mp.: 70–71° C. |
| 24 | $CH_3-$ | H | H | $OCH_3$ | $OCH_3$ | O | CH | $R_f$: 0,26 (ethyl acetate) |
| 25 | 3-Thienyl | H | $CH_3$ | $OCH_3$ | $OCH_3$ | S | CH | mp.: 81° C. |
| 26 | 3-Furyl | H | $CH_3$ | $OCH_3$ | $OCH_3$ | S | CH | mp.: 115° C. |
| 27 | N-Methyl-2-pyrrolyl | H | $CH_3$ | $OCH_3$ | $OCH_3$ | S | CH | mp.: 109° C. |
| 28 | 4-Nitrophenyl | H | $CH_3$ | $OCH_3$ | $OCH_3$ | S | CH | mp.: 148° C. |
| 29 | 2-Pyrrolyl | H | $CH_3$ | $OCH_3$ | $OCH_3$ | S | CH | mp.: 137° C. |
| 30 | 2-Pyridyl | H | $CH_3$ | $OCH_3$ | $OCH_3$ | S | CH | mp.: 110° C. |
| 31 | 3-Pyridyl | H | $CH_3$ | $OCH_3$ | $OCH_3$ | S | CH | mp.: 100° C. |
| 32 | 2-Chlorophenyl | H | $CH_3$ | $OCH_3$ | $OCH_3$ | S | CH | mp.: 100° C. |
| 33 | 3-Chlorophenyl | H | $CH_3$ | $OCH_3$ | $OCH_3$ | S | CH | mp.: 110° C. |
| 34 | 2-Methoxyphenyl | H | $CH_3$ | $OCH_3$ | $OCH_3$ | S | CH | mp.: 110° C. |
| 35 | 2-Methylphenyl | H | $CH_3$ | $OCH_3$ | $OCH_3$ | S | CH | mp.: 94° C. |
| 36 | 3-Pyridyl | H | H | $OCH_3$ | $OCH_3$ | S | CH | mp.: 190° C. (dec.) (× HCl) |
| 37 | 3-Methylphenyl | H | $CH_3$ | $OCH_3$ | $OCH_3$ | S | CH | mp.: 90° C. |
| 38 | 4-Fluorophenyl | H | $CH_3$ | $OCH_3$ | $OCH_3$ | S | CH | $n_D^{20}$: 1.5618 |
| 39 | 3-Chlorophenyl | H | H | $OCH_3$ | $OCH_3$ | S | CH | mp.: 147° C. |
| 40 | 4-Methylphenyl | H | $CH_3$ | $OCH_3$ | $OCH_3$ | S | CH | mp.: 95° C. |
| 41 | 2-Methylphenyl | H | H | $OCH_3$ | $OCH_3$ | S | CH | mp.: 200–210° C. (dec.) |
| 42 | 3-Methylphenyl | H | H | $OCH_3$ | $OCH_3$ | S | CH | mp.: 212° C. (dec.) |
| 43 | 2-Fluorophenyl | H | $CH_3$ | $OCH_3$ | $OCH_3$ | S | CH | mp.: 85° C. |
| 44 | 2-Fluorophenyl | H | H | $OCH_3$ | $OCH_3$ | S | CH | mp.: 182° C. (dec.) |
| 45 | 4-Methoxyphenyl | H | H | $OCH_3$ | $OCH_3$ | S | CH | mp.: 195° C. (dec.) |
| 46 | 4-Fluorophenyl | H | H | $OCH_3$ | $OCH_3$ | S | CH | mp.: 188° C. (dec.) |
| 47 | 4-Methoxyphenyl | H | $CH_3$ | $OCH_3$ | $OCH_3$ | S | CH | mp.: 80° C. |
| 48 | 4-Pyridyl | H | $CH_3$ | $OCH_3$ | $OCH_3$ | S | CH | mp.: 81° C. |
| 49 | Cyclohexyl | H | $CH_3$ | $OCH_3$ | $OCH_3$ | S | CH | mp.: 76–81° C. |
| 50 | $(CH_3)_3C-$ | H | $CH_3$ | $OCH_3$ | $OCH_3$ | S | CH | $n_D^{20}$: 1.5308 |
| 51 | 2-Phenylethyl | H | H | $OCH_3$ | $OCH_3$ | S | CH | $R_f$: 0 (ethyl acetate) |
| 52 | Phenyl | H | $CH_3$ | $CH_3$ | $CH_3$ | S | CH | $n_D^{20}$: 1.5978 |
| 53 | Phenyl | H | $CH_2CH_3$ | $OCH_3$ | $OCH_3$ | S | CH | $n_D^{20}$: 1.5974 |
| 54 | Phenyl | H | $CH_3$ | $OCH_3$ | $OCH_3$ | S | N | |
| 55 | Phenyl | H | H | $OCH_3$ | $OCH_3$ | S | N | |

-continued

| Example No. | A | G | R¹ | R² | R³ | X | Y | Physical constant |
|---|---|---|---|---|---|---|---|---|
| 56 | Phenyl | H | CH₃ | OCH₃ | OCH₃ | O | CH | mp.: 106-109° C. |
| 57 | Phenyl | H | H | OCH₃ | OCH₃ | O | CH | $n_D^{20}$: 1.5759 |
| 58 | Phenyl | H | CH₃ | OCH₃ | OCH₃ | O | N | |
| 59 | Phenyl | H | H | OCH₃ | OCH₃ | O | N | |
| 60 | Phenyl | H | CH₂CH₃ | OCH₃ | OCH₃ | O | CH | $n_D^{20}$: 1.5638 |
| 61 | Phenyl | H | CH₂CH₃ | OCH₃ | OCH₃ | O | N | $n_D^{20}$: 1.5535 |

The following examples illustrate the possibilities for use of the compounds of the invention.

EXAMPLE A

In a greenhouse, the noted plant species were treated post-emergently with the noted compounds of the invention, at a rate of 0.1 kg active ingredient/ha. The compounds of the invention were sprayed evenly over the plants as emulsions or suspensions in 500 liters water/ha. Two weeks after the treatment, the compounds of the invention showed a high crop selectivity in wheat and maize with excellent activity against the weeds. The comparison material did not show similar high efficacy.

In the following table:
0=no damage
1=1-24% damage
2=25-74% damage
3=75-89% damage
4=90-100% damage
TRZAX=Triticum aestivum
ZEAMX=Zea mays
GALAP=Galium aparine
SEBEX=Sesbania exaltata
SOLSS=Solanum sp.

| Compounds of invention | TRZAX | ZEAMX | GALAP | SEBEX | SOLSS |
|---|---|---|---|---|---|
| Example 1 | 0 | 0 | 3 | 3 | 3 |
| Untreated Comparison | 0 | 0 | 0 | 0 | 0 |
| Methyl 2-(4-isopropyl-4-methyl-5-oxo-2-imidazolin-2-yl)-4(5)-methylbenzoate | 0 | 0 | 1 | 1 | 0 |

EXAMPLE B

In a greenhouse, the noted plant species were treated pre-emergently with the noted compounds of the invention, at a rate of 0.1 kg active ingredient/ha. The compounds of the invention were sprayed evenly over the soil as emulsions or suspensions in 500 liters water/ha. Three weeks after the treatment, the compounds of the invention showed a high crop selectivity in wheat and maize with excellent activity against the weeds. The comparison material did not show similar high efficacy.

In the following table:
0=no damage
1=1-24% damage
2=25-74% damage
3=75-89% damage
4=90-100% damage
TRZAX=Triticum aestivum
VERPE=Veronica persica
VIOSS=Viola sp

| Compounds of invention | TRZAX | VERPE | VIOSS |
|---|---|---|---|
| Example 13 | 0 | 3 | 3 |
| Example 25 | 0 | 3 | — |
| Untreated Comparison | 0 | 0 | 0 |
| Methyl 2-(4-isopropyl-4-methyl-5-oxo-2-imidazolin-2-yl)-4(5)-methylbenzoate | 0 | 1 | 2 |

We claim:
1. Substituted pyrimidinyloxy(thio) acrylic acid compound of formula I

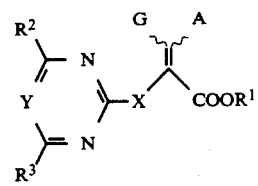
(I)

in which
A is one of the groups A-1 to A-6 of formula

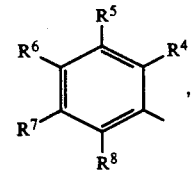
A-1

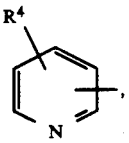
A-2

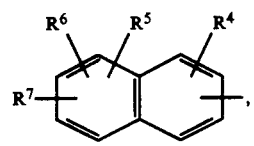
A-3

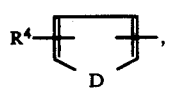
A-4

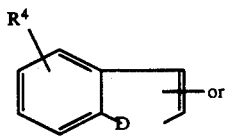
A-5

-continued

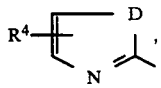
A-6 a $C_1$-$C_{10}$-alkyl, $C_2$-$C_{10}$-alkenyl or $C_2$-$C_{10}$-alkynyl group (each of which is optionally substituted by one or more of the same or different $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl), or a $C_3$-$C_8$-cycloalkyl or $C_4$-$C_8$-cycloalkenyl group (each of which is optionally substituted by one or more of the same or different $C_1$-$C_4$-alkyl, $C_1$-$C_4$-alkoxy, $C_1$-$C_4$-alkylthio, amino, $C_1$-$C_4$-alkylamino, di-$C_1$-$C_4$-alkylamino, nitro, trifluoromethyl, halogen or phenyl);

D is oxygen, sulphur or the group $-NR^9-$;

G is hydrogen or $C_1$-$C_6$-alkyl;

$R^1$ is hydrogen, $C_1$-$C_4$-alkyl or benzyl;

$R^2$ and $R^3$, which may be the same or different, are $C_1$-$C_4$-alkyl, $C_1$-$C_4$-alkoxy, $C_1$-$C_4$-alkylthio, $C_1$-$C_4$-alkylamino, di-$C_1$-$C_4$-alkylamino or halogen;

$R^4$, $R^5$, $R^6$, $R^7$ and $R^8$, which may be the same or different, are hydrogen, $C_1$-$C_4$-alkyl, $C_1$-$C_4$-alkoxy, amino, di-$C_1$-$C_4$-alkylamino, nitro, halogen, trifluoromethyl or phenyl;

$R^9$ is hydrogen, $C_1$-$C_4$-alkyl or phenyl;

X is oxygen or sulphur; and

Y is methine;

as well as their alkali metal, alkaline earth metal and organic ammonium salts, and their E- and Z-isomers 2. A herbicidal composition which comprises a compound according to claim 1, in admixture with in admixture with agriculturally acceptable carriers or diluents.

3. A method of combating weeds which comprises applying to the weeds or their locus a compound according to claim 1.

4. Compound according to claim 1 in which X is S.

5. Compound according to claim 4 in which A is A-1.

6. Compound according to claim 4 in which $R^2$ and $R^3$ are alkoxy and in which $R^1$ is hydrogen or methyl.

7. Compound according to claim 6 in which $R^2$ and $R^3$ are methoxy and G is hydrogen.

8. Compound according to claim 7 in which A is A-1, A-3, or A-4, $R^4$-$R^8$ are hydrogen and D is S.

9. Compound according to claim 1 in which X is O.

10. A herbicidal composition which comprises a compound according to claim 4, in admixture with agriculturally acceptable carriers or diluents.

11. A herbicidal composition which comprises a compound according to claim 5, in admixture with agriculturally acceptable carriers or diluents.

12. A herbicidal composition which comprises a compound according to claim 7, in admixture with agriculturally acceptable carriers or diluents.

13. A herbicidal composition which comprises a compound according to claim 8, in admixture with agriculturally acceptable carriers or diluents.

14. A method of combating weeds which comprises applying to the weeds or their locus a compound according to claim 4.

15. A method of combating weeds which comprises applying to the weeds or their locus a compound according to claim 5.

16. A method of combating weeds which comprises applying to the weeds or their locus a compound according to claim 7.

17. A method of combating weeds which comprises applying to the weeds or their locus a compound according to claim 8.